United States Patent [19]

Bruchmüller

[11] Patent Number: 4,532,806
[45] Date of Patent: Aug. 6, 1985

[54] SENSOR FOR MONITORING THE DEPOSITION OF FROZEN FOG AND/OR ICE ON SURFACES

[75] Inventor: Hans-George Bruchmüller, Giengen, Fed. Rep. of Germany

[73] Assignee: Bosch-Siemens Hausgeraete GmbH, Munich, Fed. Rep. of Germany

[21] Appl. No.: 466,546

[22] Filed: Feb. 15, 1983

[30] Foreign Application Priority Data

Feb. 16, 1982 [DE] Fed. Rep. of Germany ....... 3205370

[51] Int. Cl.³ ............................................. G01N 29/00
[52] U.S. Cl. ........................................ 73/579; 73/590; 340/582; 62/140
[58] Field of Search ......................... 73/590, 599, 579; 340/582; 62/140

[56] References Cited

U.S. PATENT DOCUMENTS 4,176,524 12/1979 Kamiyama et al. .................. 340/582
4,335,613 6/1982 Luukkala .............................. 73/599

Primary Examiner—Anthony V. Ciarlante
Attorney, Agent, or Firm—Herbert L. Lerner; Laurence A. Greenberg

[57] ABSTRACT

A sensor for monitoring the deposition of frozen fog and/or ice on evaporator, refrigeration machine or heat pump surfaces, includes a can-shaped housing having opposite sides. A mounting heat conductingly connects the housing to the evaporator. First and second membranes are respectively disposed at the opposite sides of the housing, and first and second electro-acoustic transducers are each attached to a respective one of the membranes. An alternating voltage is applied to the first transducer causing the first transducer to oscillate the first membrane, and the second membrane is spaced from the first membrane by a distance permitting oscillation of the first membrane to oscillate the second membrane.

8 Claims, 4 Drawing Figures

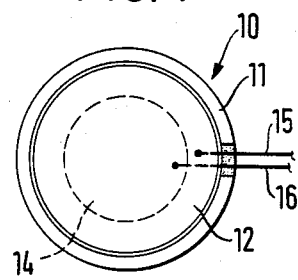
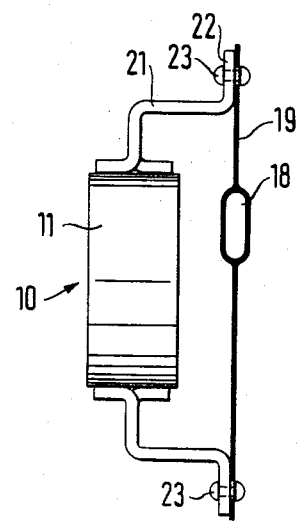
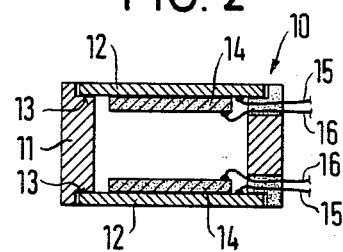
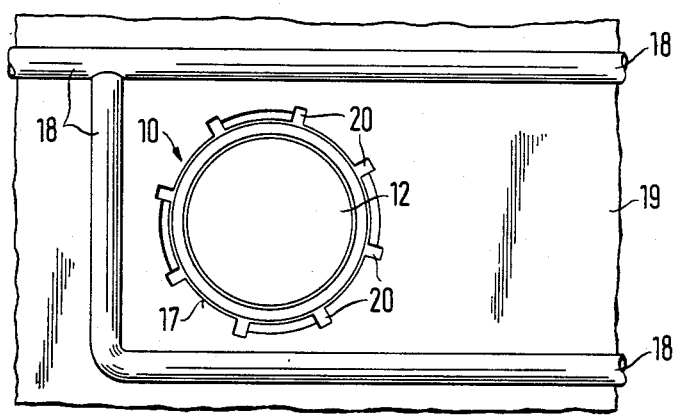

SENSOR FOR MONITORING THE DEPOSITION OF FROZEN FOG AND/OR ICE ON SURFACES

The invention relates to a sensor for monitoring the deposition of frozen fog and/or ice on surfaces, especially on surfaces of evaporators, refrigeration machines, heat pumps or the like, in the form of a can-shaped housing which can be attached to an evaporator with a heat conducting contact mounting, the housing having a membrane to which an electro-acoustic transducer is attached, the transducer being able to oscillate by applying an alternating voltage, and the transducer being a piezo-electric element or the like.

A prior art sensor of this type, disclosed in German Pat. No. DE-PS 27 50 165, includes a membrane carrying the electro-acoustic transducer which is heat-conductingly connected to a base plate by an elastic bellows, the base plate being fastenable to an evaporator surface with a heat conducting contact. In this arrangement, when frozen fog (frosting) forms on the membrane, a damping effect takes place, which increases with increasing thickness of the ice coating. As the damping of the membrane increases in the described manner, the impedance of the electro-acoustic transducer which is arranged in an oscillator circuit, increases also.

Due to its specific construction this known sensor is only capable of indicating relatively coarse changes of the initially amorphous deposition or frozen fog. Therefore, it can resolve the frosting process only when the layer of frozen fog is already rather thick, and begins to change to a coating of solid ice. However, because of the already considerably reduced heat transfer at the evaporator, the energy consumption of the refrigeration machine is greatly increased. Furthermore, the circuit of the electric tranducer in this case permits only a differentiation between the states "not frosted" and "already strongly frosted", so that this known sensor does not have the capability of monitoring the forming and growing of a layer of frozen fog with sufficient analogue accuracy.

Therefore, the invention has the basic objective to construct a sensor of the above-described type which is sensitive enough to be capable of indicating even the slightest formation of frozen fog, and/or of registering small changes of the frost or ice depositions with great accuracy.

This objective is achieved according to the instant invention, by the provision that the housing is provided with a second membrane also having an electro-acoustic transducer at the opposite housing side, whereby the second membrane is closely spaced from the first one, and is caused to oscillate by the transfer of the excitement of the latter.

Due to the construction of the sensor according to the invention, the vibration energy generated by the membrane used as a transmitter is transferred by body and/or air sound transmission to the membrane serving as the receiver, which thereby is excited to oscillate itself. In this manner, the alternating voltage generated by the electro-acoustic transducer disposed on the membrane serving as a receiver, is utilized as the signal for regulating the defrosting control. Since with the construction of the sensor according to the invention, frosting is deposited on both membranes, the damping effect caused thereby is doubly effective, so that this sensor has the capability of especially sensitively indicating even the slightest deposition of frozen fog, and/or the smallest changes of the frost deposit. The sensor is thereby capable of optimally controlling a defrosting process or of operating a warning device with great reliability and accuracy.

An especially advantageous effect is obtained, if according to a preferred embodiment of the invention, it is provided that the second membrane is at least approximately parallel to the first membrane at the housing.

According to a further advantageous embodiment of the invention, it is provided that the electro-acoustic transducers are made as piezo-ceramic oscillators, which cover the central region of the membrane up to close to a location its edge, and whose resonant frequencies are almost identical.

Additional advantageous features of the sensor according to the invention are described in the claims, and will be explained below with the aid of a typical embodiment, which is schematically shown in the drawing.

FIG. 1 shows a sensor formed of a ring-shaped housing with two membranes at its ends, seen in the axial direction of the housing, FIG. 2 shows an axial section through the sensor according to FIG. 1, FIG. 3 shows a first typical embodiment, wherein the sensor is disposed in a perforation of an evaporator plate and is shown in a part of the evaporator plate, FIG. 4 shows another typical embodiment with a sensor which is fastened to the evaporator plate by a special holding arrangement.

A sensor for monitoring the formation of frozen fog and/or ice deposits on surfaces is designated by reference numeral 10 in FIGS. 1 to 4, and is constructed with a can-shaped housing 11 in the form of a hollow cylinder with an annular cross-section. The housing 11 which is made of a material with good thermal conduction, for example, Al, Cu or the like, is closed by a circular membrane 12 at each of its end-sides. The membrane is set into a step-like recess 13 at the axial end sides of the housing 11 in the embodiment shown, and can be secured there by cementing, for example, or by similar means.

At the inside of the membrane 12, which preferably is made of metallic material having good electrical and thermal conductivity and being able to vibrate, an electro-acoustic transducer 14 is provided. The latter is made in the form of a circular disc of a piezo-ceramic material, which covers the center region of the membrane 12 close to its edge. The electro-acoustic transducer 14 is fastened to the membrane 12 by cementing, for example. Electrical lines 15 and 16 are connected in a conventional manner to the endsides of the electro-acoustic transducer 14 serving as connection terminals, whereby the line 16 is directly attached to the surface of the electro-acoustic transducer serving as the electrode, while the line 15 is in an electrically conducting connection with the other electrode of the electro-acoustic transducer 14 through the membrane. The connection lines 15 and 16 are conducted to the outside through perforations in the wall of the housing 11, which are air tightly closed by a suitable sealing compound.

In the embodiment shown in FIG. 3, the sensor 10 is attached with a thermally well conducting connection in a circular perforation 17 of an evaporator-plate 19, which is provided with channels 18 for the cooling medium. Thereby, the two membranes 12 lie approximately parallel to the surface of the evaporator plate 19, and are almost equally spaced away from the latter. The edge of the perforation 17 which contains the sensor 10 is provided with radial cut-outs 20 spaced at regular distances from each other, so that lugs are formed which project alternatingly from opposite sides of the evaporator plate 19. In this manner a thermally well conducting connection is established between the evaporator plate 19 and the housing 11 of the sensor 10.

In the embodiment shown in FIG. 4, the sensor 10 is retained with its housing 11 in a holding element 21, which is provided with a flange-like rim 22, and is fastened to the evaporator plate 19 by rivets 23, for example. In this case, the distance from the sensor 10 to the surface of the evaporator plate 19 is chosen as small as possible while still permitting water drops running downward on the evaporator plate surface to drain off unobstructed, without being trapped between the evaporator plate 19 and the membrane 12 of the sensor 10 which is facing the plate.

In the described and illustrated embodiment, one of the electroaccoustic transducers 14 is operated as a transmitter, while the other serves as a receiver. For example, the transmitter is excited by a constant sinusoidal alternating voltage with about 20 V peak potential, whose frequency corresponds to the lowest resonant frequency of the system. This frequency lies about in the range of three to four KHz. The transmitter which is operated in this manner, generates sound waves, which excite the oppositely positioned membrane 12 which serves as a receiver, through the enclosed air volume. Some vibration (sound) is also transferred to the receiver through the housing 11 which is constructed in the form of a ring. The receiver whose own resonant frequency is about the same as the frequency of the transmitter, thus generates an alternating voltage with the exciting frequency, whose amplitude in the unloaded case is the same or slightly lower than the exciting voltage, and in the case of resonant magnification can also be slightly greater than the excitement voltage. Due to the frozen fog formation on the two membranes 14 caused by the operation of the refrigeration machine, the lowest resonant frequency of the system is shifted about 100 to 1000 Hz. However when ice is formed, the frequency is increased upward by 3000 Hz. Additionally, a thin layer of ice also strongly dampens the system. Due to both effects, the level of the output voltage of the unloaded system excited at the resonant frequency is markedly lower.

Experiments have shown that in comparison to the output voltage $U_o$ of the unloaded system, the output level with a thin water film drops about 10 dB, whereas during the slight formation of frozen fog, the output level drops about 20 dB. During the strong formation of frozen fog, the output level sinks about 30 dB, and with a layer of ice of about 1 mm thickness, the drop is about 40 dB, while it sinks by more than 50 dB with very strong icing. Thereby, the formula applies:

$$L = 20 \log (U/U_o) \, dB$$

where L is the output level in decibels, $U_o$ is the output voltage of the unloaded system, and U is the output voltage of the loaded system.

The change of voltage ratios due to the frosting or icing of the membranes is so great that it is possible to correspondingly regulate the refrigeration cycle with suitable deicing or defrosting periods with a simple electronic circuit, for example, using a threshold switch.

The illustrated and described sensor 10 should be installed at a location in the evaporator of a refrigeration device where the frosting or icing is to be controlled. It is important to provide a reliable thermal contact at the installation, which can be achieved by the above-described measures. However, the holding provisions must not inhibit the free vibration of the membranes 12. Additionally, the membranes 12 must not touch the evaporator 19. If the sensor is attached according to FIG. 4, the membrane 14 which is turned toward the evaporator 19 should be spaced from the surface of the evaporator just far enough, so that a water drop which runs down along the evaporator just clears the membrane.

I claim:

1. Sensor for monitoring the deposition of frozen fog and/or ice on evaporator surfaces, comprising a can-shaped housing having opposite sides, means for heat conductingly connecting said housing to the evaporator, first and second membranes respectively disposed at said opposite sides of said housing, first and second electroacustic transducers each being attached to a respective one of said membranes, and means for applying alternating voltage to said first transducer causing said first transducer to oscillate said first membrane, said second membrane being spaced from said first membrane by a distance permitting oscillation of said first membrane to oscillate said second membrane.

2. Sensor according to claim 1, wherein said transducers are piezo-electric elements.

3. Sensor according to claim 1, wherein said membranes are substantially mutually parallel and congruent.

4. Sensor according to claim 1, wherein said transducers are piezo-ceramic oscillators having substantially identical resonant frequencies, said oscillators being centrally disposed on said membrane and being extended to the vicinity of the edges of said membrane.

5. Sensor according to claim 4, wherein said oscillators are circular and have smaller surface areas than said membranes.

6. Sensor according to claim 1, wherein said housing is mounted in a cutout formed in the evaporator and said membranes are substantially parallel to the evaporator surface.

7. Sensor according to claim 1, wherein said connecting means are holding elements attaching said housing substantially parallel to and in vicinity of the evaporator.

8. Sensor according to claim 1, wherein said housing is a cylinder having an annular cross section, said opposite sides of said housing being ends of said cylinder to which said membranes are attached.

* * * * *